US00PP33737P2

(12) United States Plant Patent
Hernandez et al.

(10) Patent No.: US PP33,737 P2
(45) Date of Patent: Dec. 14, 2021

(54) STRAWBERRY PLANT NAMED 'DRISSTRAWEIGHTYFOUR'

(50) Latin Name: ***Fragaria* x *ananassa***
Varietal Denomination: DrisStrawEightyFour

(71) Applicant: Driscoll's, Inc., Watsonville, CA (US)

(72) Inventors: Maria Cruz Ayuso Hernandez, Watsonville, CA (US); Katalin M. Pakozdi, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/926,321

(22) Filed: Jul. 10, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 6/7409
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson et al.
PP22,247 P2 11/2011 Ferguson (Continued)

OTHER PUBLICATIONS

U.S. Appl. No. 16/912,523, filed Jun. 25, 2020 titled "Strawberry Plant Variety Named Drisstraweightytwo".

(Continued)

*Primary Examiner* — Anne Marie Grunberg
(74) *Attorney, Agent, or Firm* — Morrison & Foerster LLP

(57) ABSTRACT

A new and distinct variety of strawberry plant named 'DrisStrawEightyFour', particularly selected for its medium-sized plant with long trusses, its conic fruit with bright, intense red color, as well as its very early maturity, is disclosed.

9 Drawing Sheets

(56) References Cited

U.S. PATENT DOCUMENTS

| | | | |
|---|---|---|---|
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| 2003/0079263 | P1 | 4/2003 | Gilford et al. |
| 2013/0276182 | P1 | 10/2013 | Fear et al. |

OTHER PUBLICATIONS

Unpublished U.S. Appl. No. 16/873,276, filed Mar. 10, 2020, titled Strawberry Plant Variety Named 'Drisstraweighty'.

Unpublished U.S. Appl. No. 16/873,277, filed Mar. 10, 2020, titled Strawberry Plant Variety Named 'Drisstraweightyone'.

Unpublished U.S. Appl. No. 16/912,629, filed Jun. 25, 2020, titled Strawberry Plant Variety Named 'Drisstraweightythree'.

Ferguson et al., "Unpublished U.S. Appl. No. 16/501,428, filed Apr. 12, 2019, titled "Strawberry Plant Variety Named 'Drisstrawseventyfive'"".

Ferguson et al., "Unpublished U.S. Appl. No. 16/501,759, filed Jun. 4, 2019, titled "Strawberry Plant Variety Named 'Drisstrawseventyseven'"".

Ferguson et al., "Unpublished U.S. Appl. No. 16/602,701, filed Nov. 22, 2019, titled Strawberry Plant Variety Named Drisstrawsixtynine".

Jacobs et al., "Unpublished U.S. Appl. No. 16/501,501, filed Apr. 18, 2019, titled "Strawberry Plant Variety Named 'Drisstrawseventy'"".

Mendoza et al., "Unpublished U.S. Appl. No. 16/350,139, filed Oct. 2, 2018, titled "Strawberry Plant Variety Named 'Drisstrawsixtyseven'"".

Mendoza,"Unpublished U.S. Appl. No. 16/501,602, filed May 7, 2019, titled "Strawberry Plant Variety Named 'Drisstrawsixtyeight'"".

Mendoza et al., "Unpublished U.S. Appl. No. 16/501,849, filed Jun. 18, 2019, titled "Strawberry Plant Variety Named 'Drisstrawseventyeight'"".

Mendoza et al., "Unpublished U.S. Appl. No. 16/602,476, filed Oct. 15, 2019, titled Strawberry Plant Variety Named Drisstrawseventynine".

Pakozdi et al., "Unpublished U.S. Appl. No. 16/501,198, filed Mar. 5, 2019, titled "Strawberry Plant Variety Named 'Drisstrawseventythree'"".

Stewart et al., "Unpublished U.S. Appl. No. 16/501,449, filed Apr. 17, 2019, titled "Strawberry Plant Variety Named 'Drisstrawseventyone'"".

STRAWBERRY PLANT NAMED 'DRISSTRAWEIGHTYFOUR'

Latin name: Botanical classification: *Fragaria* x *ananassa*.

Varietal denomination: The varietal denomination of the claimed variety of strawberry plant is 'DrisStrawEighty-Four'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawEightyFour'.

Strawberry plant variety 'DrisStrawEightyFour' originated from a cross between the proprietary female parent '974AC033' (unpatented) and the proprietary male parent 'ES089.028' (unpatented). Progeny plants from this cross of '974AC033' x 'ES 089.028', including 'DrisStrawEighty-Four', were asexually propagated via stolons in Valladolid, Spain in August of 2018. Strawberry plant variety 'DrisStrawEightyFour' was later specifically identified and selected in Huelva, Spain in 2019.

'DrisStrawEightyFour' was subsequently asexually propagated via stolons, and has undergone testing at test plots in Huelva, Spain for two years (2018 to 2020). The present variety has been found to be stable and reproduce true to type through successive asexual propagations via stolons and tissue culture.

'DrisStrawEightyFour' was particularly selected for its medium-sized plant with long trusses, its conic fruit with bright, intense red color, as well as its very early maturity.

DESCRIPTION OF THE DRAWINGS

This new strawberry plant is illustrated by the accompanying photographs. The colors shown are as true as can be reasonably obtained by conventional photographic procedures. Unless otherwise indicated, the photographs are of plants that are four to five months old from planting.

DETAILED BOTANICAL DESCRIPTION

Figure 1:
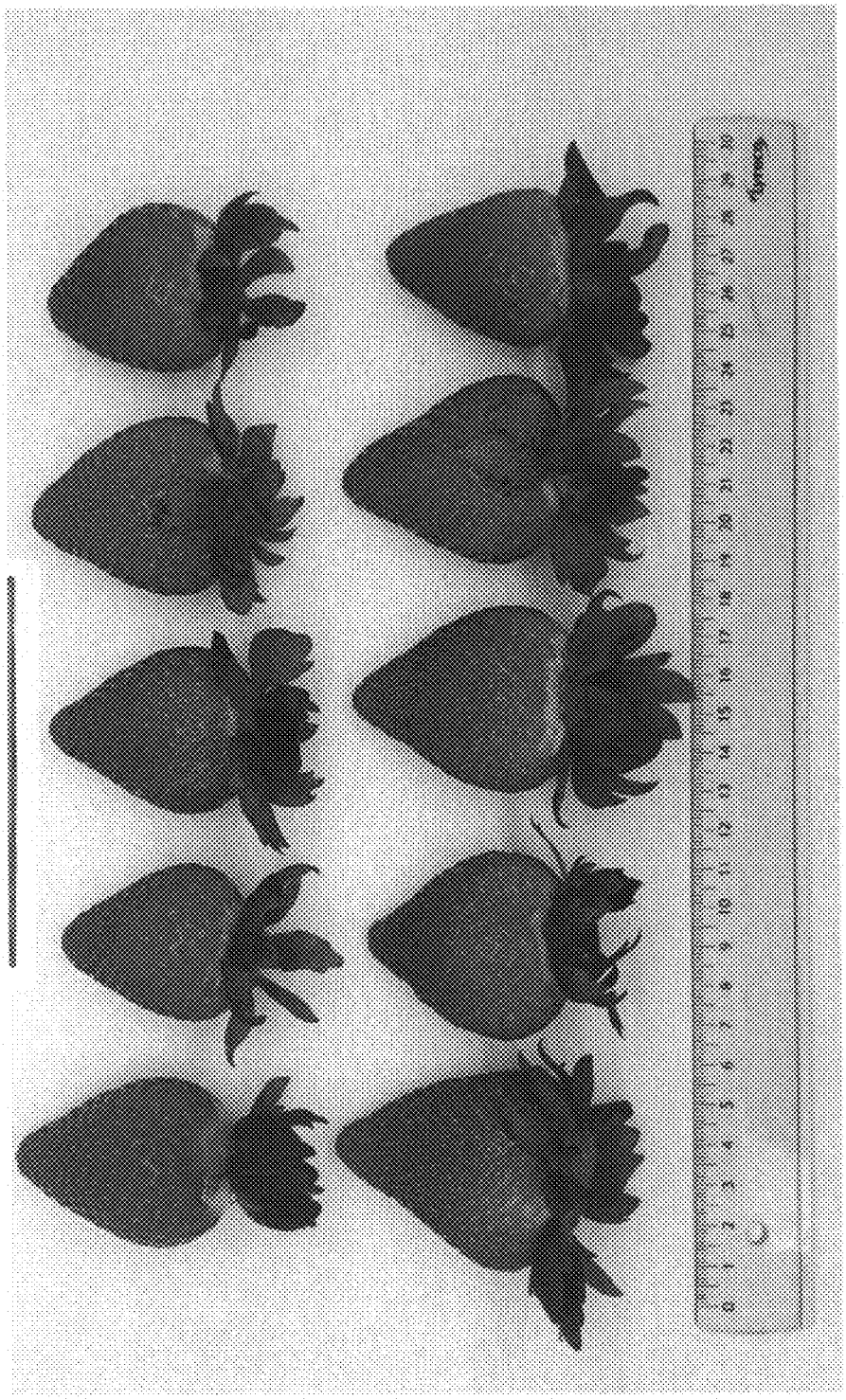
FIG. 1 illustrates whole fruit of variety 'DrisStrawEighty-Four'.
Figure 2:
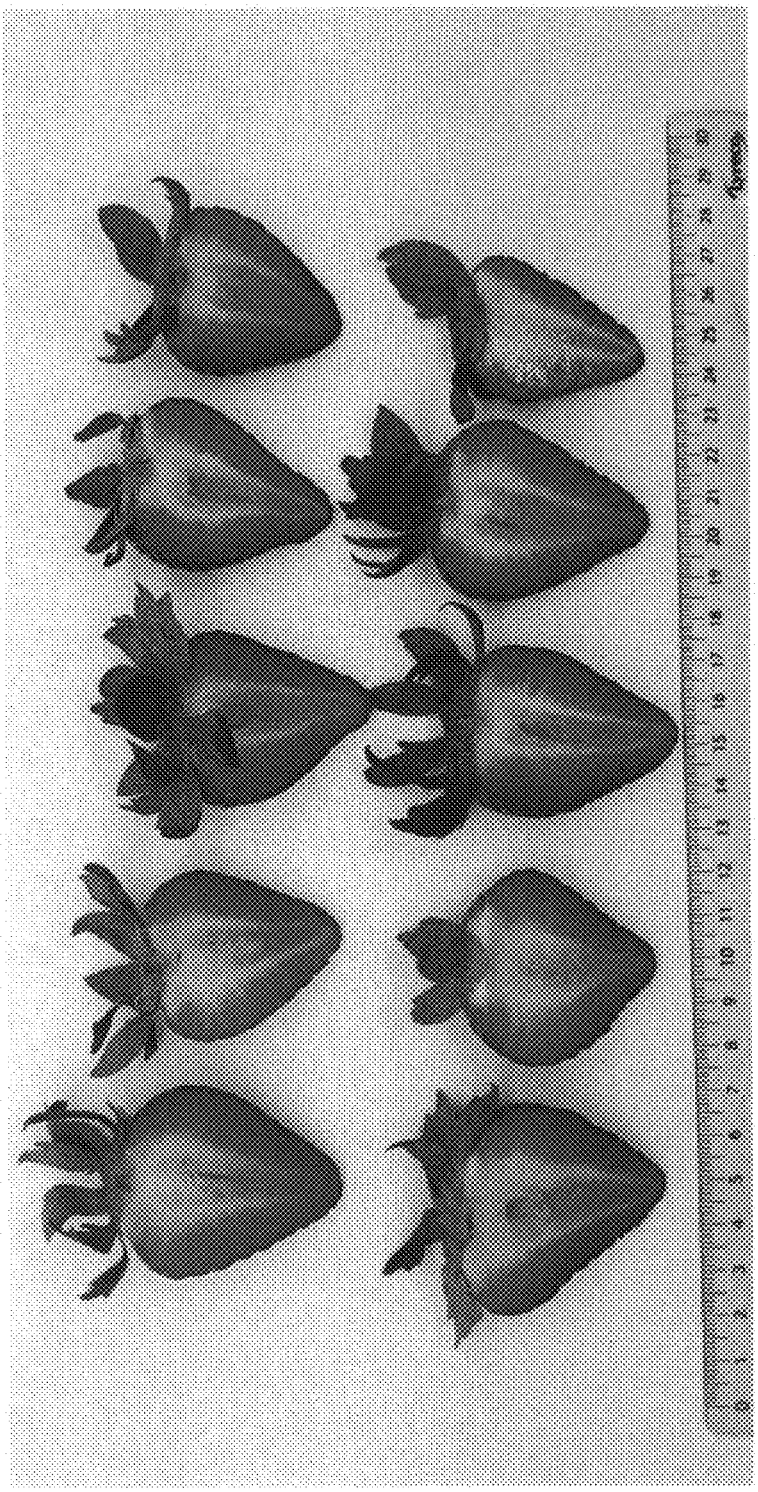
FIG. 2 illustrates longitudinal sections of fruit of variety 'DrisStrawEightyFour'.
Figure 3:
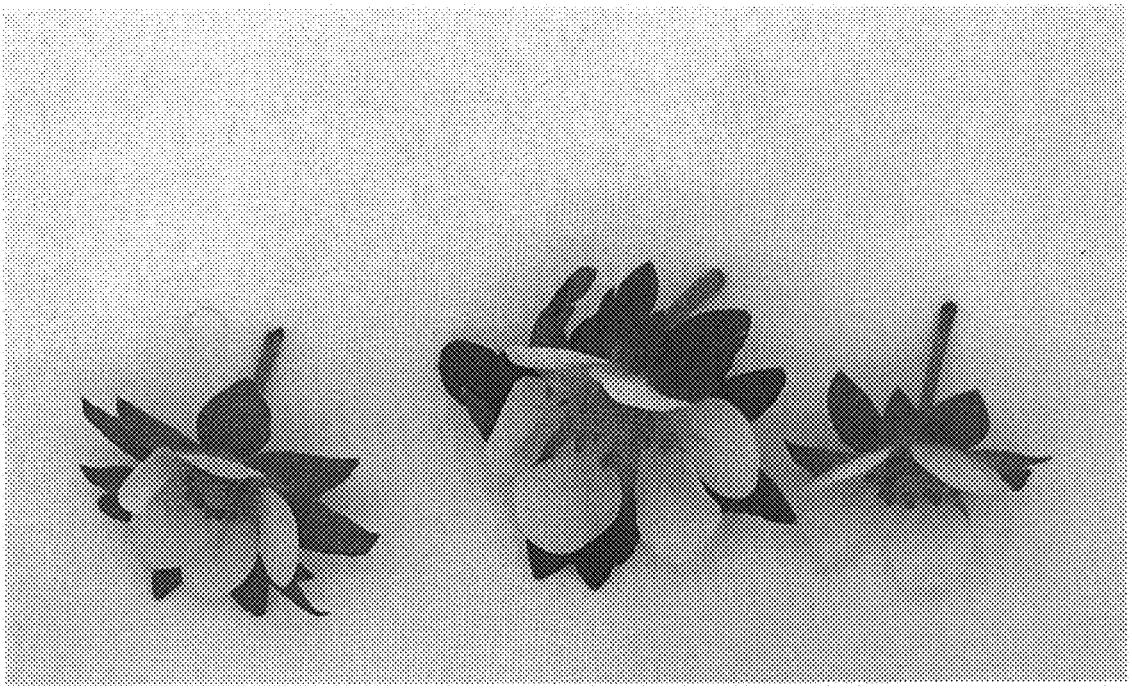
FIG. 3 illustrates the upper surface of flowers of variety 'DrisStrawEightyFour'.
Figure 4:
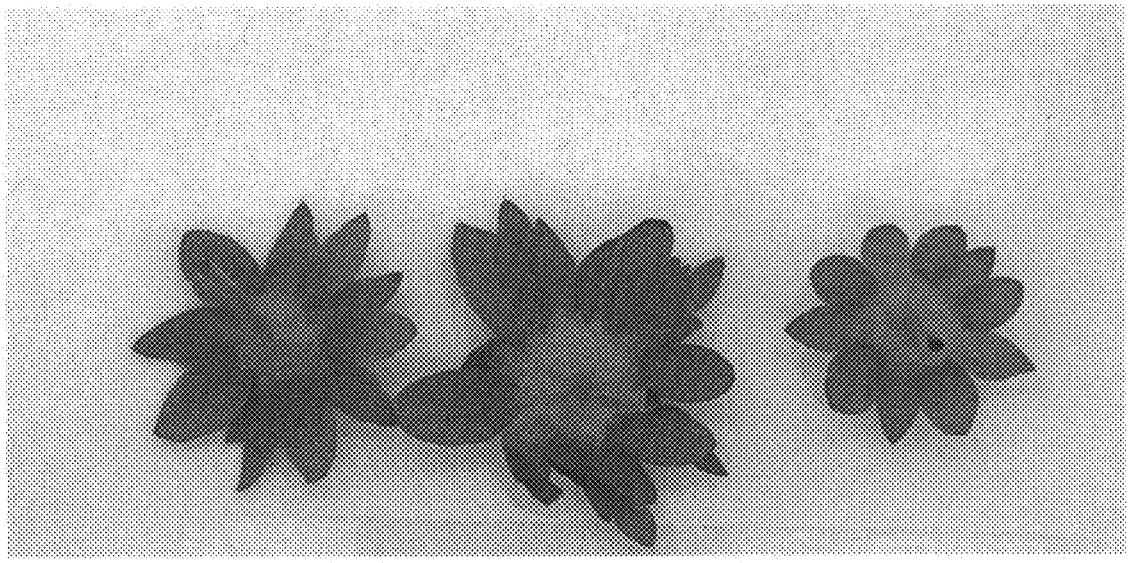
FIG. 4 illustrates the lower surface of flowers of variety 'DrisStrawEightyFour'.
Figure 5:
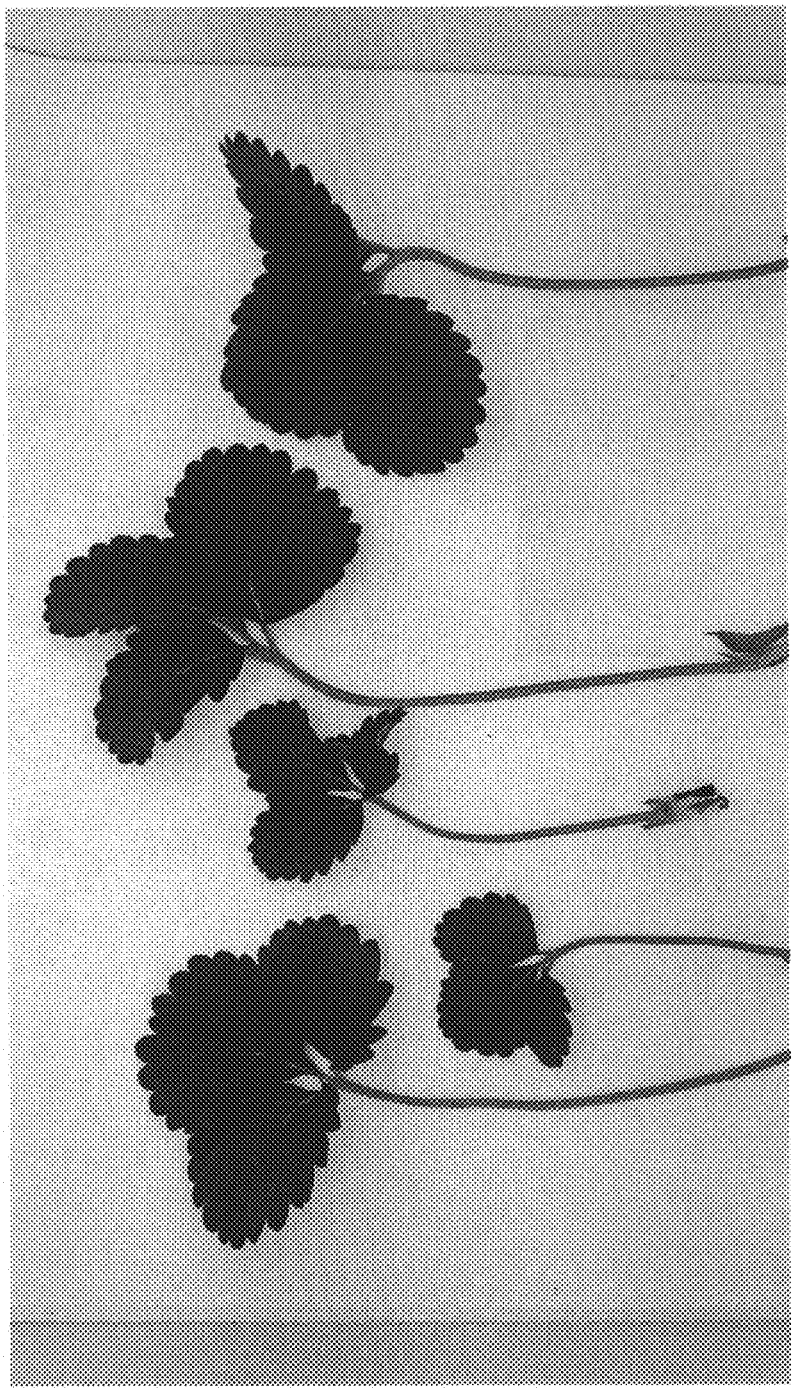
FIG. 5 illustrates the upper surface of leaves of variety 'DrisStrawEightyFour'.
Figure 6:
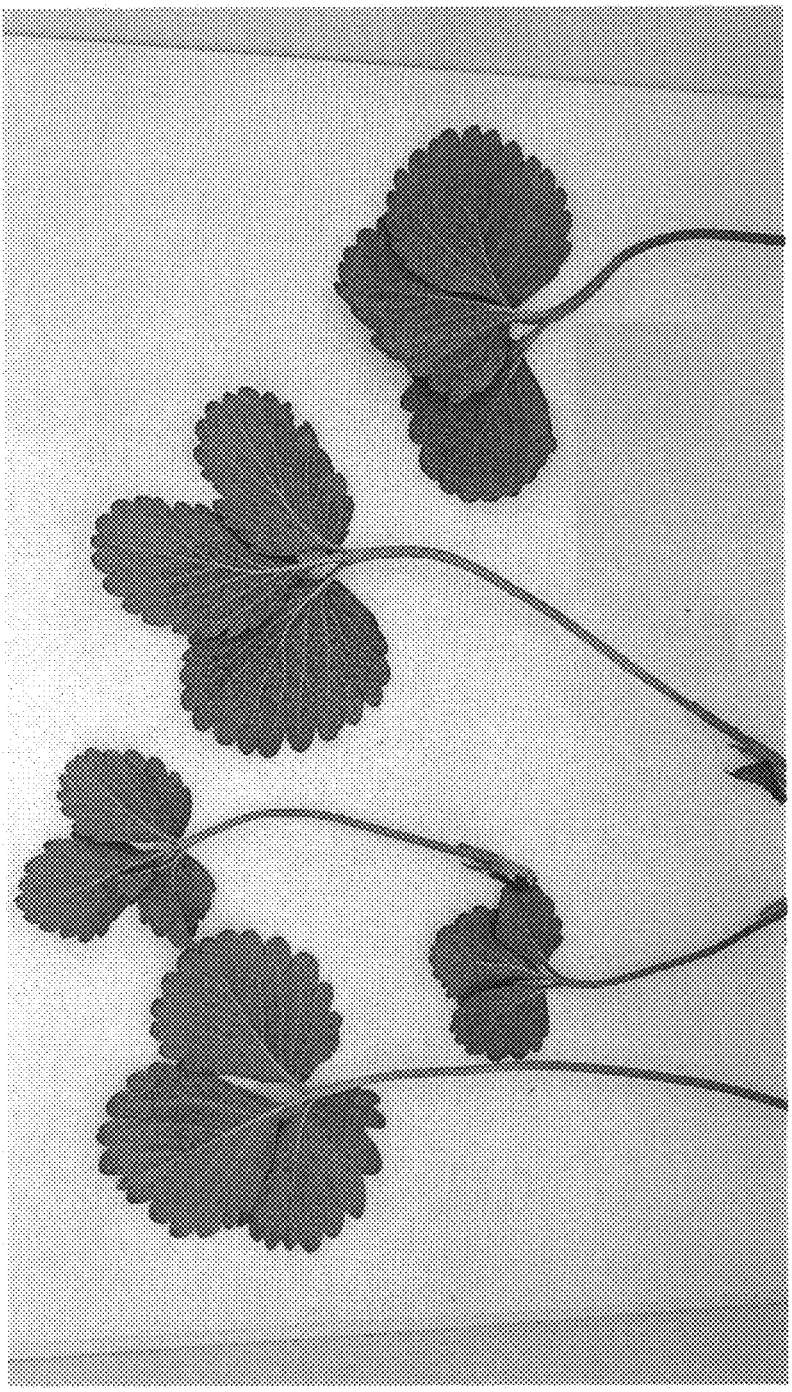
FIG. 6 illustrates the lower surface of leaves of variety 'DrisStrawEightyFour'.
Figure 7:
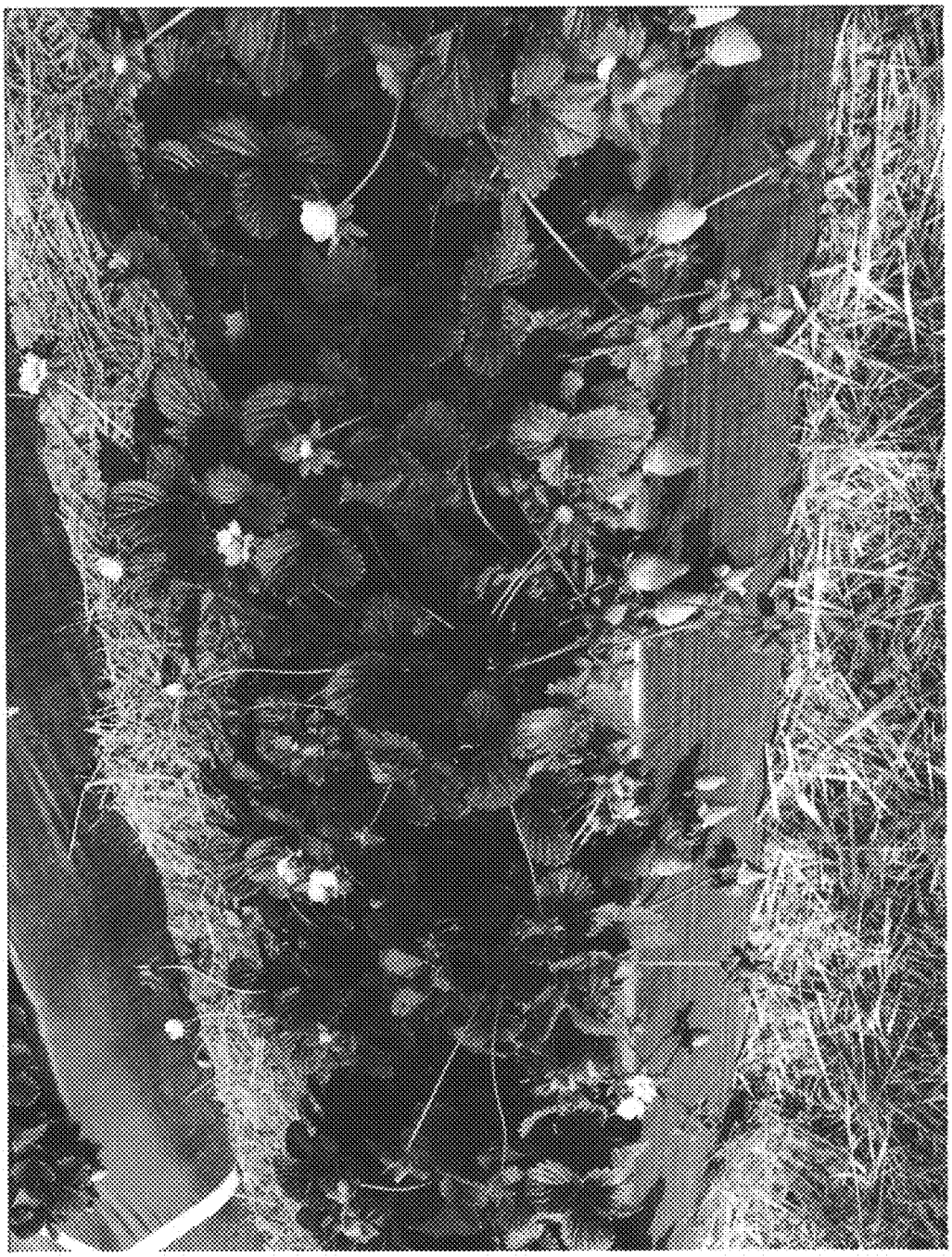
FIG. 7 illustrates 3-month-old whole plants of variety 'DrisStrawEightyFour'.
Figure 8:
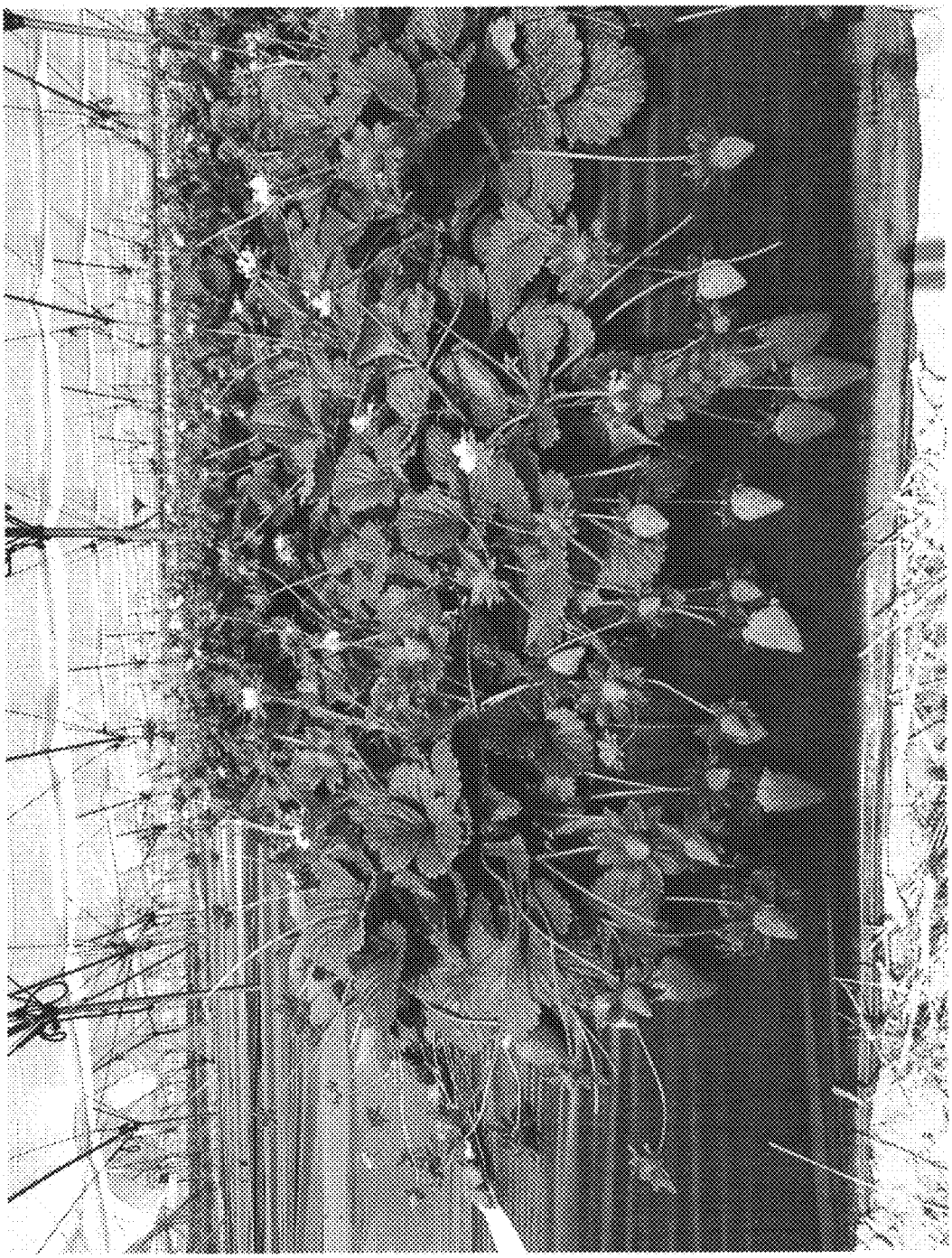
FIG. 8 illustrates 5-month-old whole plants of variety 'DrisStrawEightyFour'.
Figure 9:
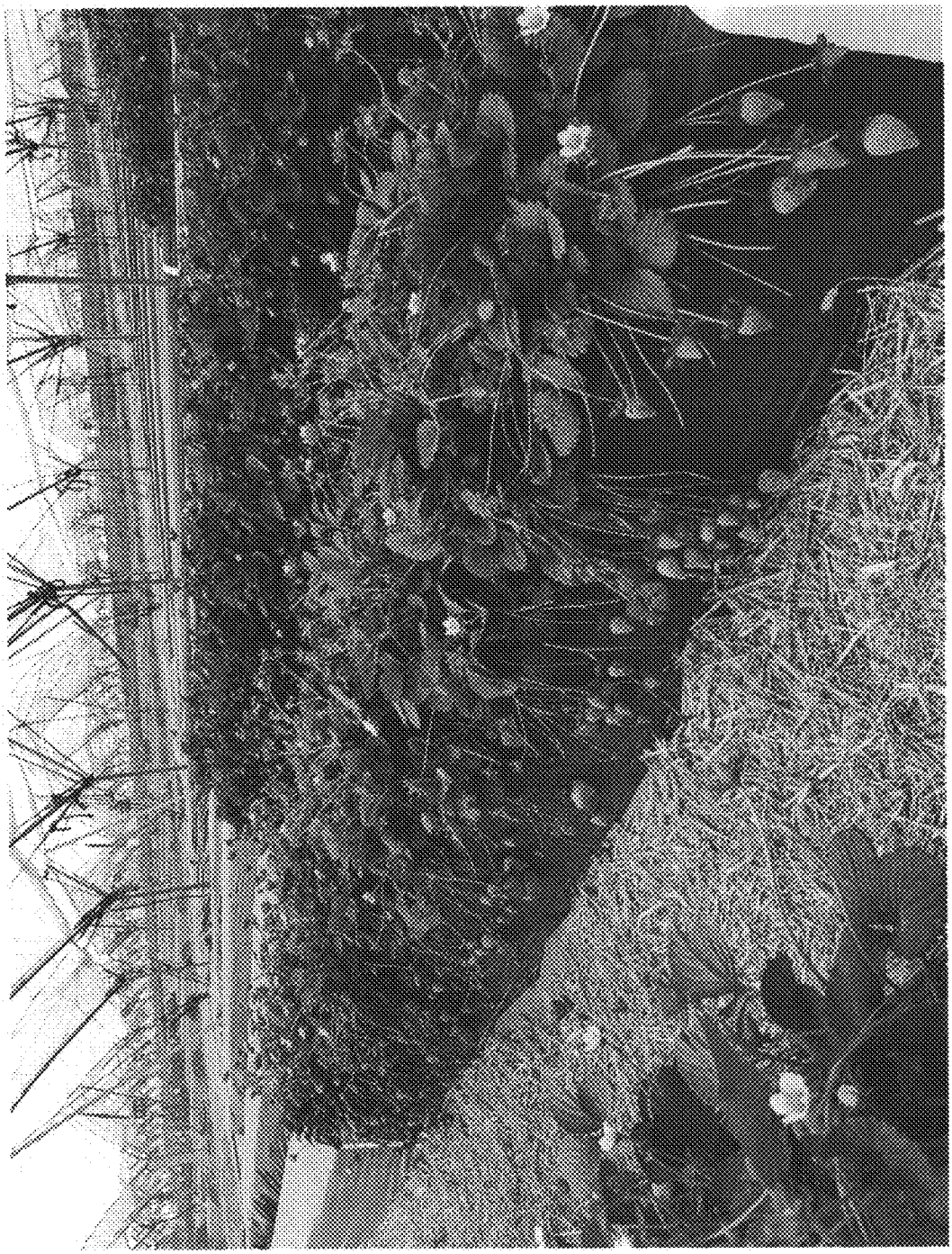
FIG. 9 illustrates 8-month-old whole plants of variety 'DrisStrawEightyFour'.

The following detailed descriptions set forth the distinctive characteristics of 'DrisStrawEightyFour'. The data which define these characteristics is based on observations taken in Huelva, Spain. This description is in accordance with UPOV terminology. Color designations, color descriptions, and other phenotypical descriptions may deviate from the stated values and descriptions depending upon variation in environmental, seasonal, climatic, and cultural conditions. 'DrisStrawEightyFour' has not been observed under all possible environmental conditions. The botanical description of 'DrisStrawEightyFour' was taken from plants that were four to five months old from planting. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary*, 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawEightyFour'.

Parentage:

*Female parent.*—Proprietary strawberry plant '974AC033' (unpatented).

*Male parent.*—Proprietary strawberry plant 'ES089.028' (unpatented).

Plant:

*Height.*—18.6 cm.

*Diameter.*—33.5 cm.

*Height/width ratio.*—0.55.

*Number of crowns per plant.*—4.1.

*Growth habit.*—Semi-upright.

*Density of foliage.*—Dense.

*Vigor.*—Medium.

Stolon:

*Average number of stolons per plant.*—8.54.

*Stolon color.*—RHS 145A (Strong yellow-green).

*Anthocyanin coloration.*—Medium.

*Stolon color with anthocyanin coloration.*—RHS 174B (Greyish reddish orange).

*Density of pubescence.*—Medium.

Fruiting truss:
*Attitude at first picking*.—Prostrate.
Leaf:
*Leaf length* (*all leaflets together, excluding petiole and stipules*).—9.5 cm.
*Leaf width* (*all leaflets together, excluding petiole and stipules*).—15.6 cm.
*Number of leaflets*.—Three only.
*Color of leaf upper surface*.—RHS 147A (Moderate olive green).
*Color of leaf lower surface*.—RHS 138B (Moderate yellow-green).
*Blistering*.—Medium.
*Glossiness*.—Absent or weak.
*Variegation*.—Absent.
Terminal leaflet:
*Length*.—5.69 cm.
*Width*.—5.41 cm.
*Length/width ratio*.—1.05.
*Length in relation to width*.—Moderately longer.
*Shape*.—Orbicular.
*Number of teeth per terminal leaflet*.—15.1.
*Shape of base*.—Obtuse.
*Shape of apex*.—Rounded.
*Margin*.—Crenate.
*Margin profile*.—Revolute (margins rolled backwards).
*Shape in cross section*.—Concave.
Petiole.—
*Length*.—126.2 mm; medium.
*Diameter*.—2.52 mm.
*Color*.—RHS 145B (Light yellow-green).
*Pubescence*.—Sparse.
*Attitude of hairs*.—Horizontal.
*Bract frequency* (*number present on each petiole*).—2.
Petiolule:
*Length*.—7.1 mm.
*Diameter*.—1.63 mm.
*Color*.—RHS 145A (Strong yellow-green).
Stipule:
*Length*.—22.4 mm.
*Width*.—5.9 mm.
*Pubescence*.—Absent or very sparse.
*Color*.—RHS 144B (Strong yellow-green).
*Anthocyanin coloration*.—Weak.
*Anthocyanin color*.—RHS 52D (Strong pink).
Inflorescence:
*Average number of flowers per flowering truss*.—1.
*Position of inflorescence in relation to foliage*.—Above.
Pedicel:
*Attitude of hairs*.—Upwards.
Flower:
*Flower diameter* (*petal tip to petal tip on non-flattened flower*).—38.6 mm.
*Arrangement of petals*.—Touching.
*Calyx diameter*.—51.8 mm.
*Size of calyx in relation to corolla*.—Larger.
*Diameter of inner calyx relative to outer*.—Same size.
*Receptacle color*.—RHS 162B (Moderate yellow).
*Stamen*.—Present.
*Anther color*.—RHS 163B (Strong orange yellow).
*Pollen*.—Color: RHS 163B (Strong orange-yellow).
*Ovary*.—Length: 12.5 mm. Diameter: 8.1 mm. Color: RHS 151C (Strong greenish yellow).
*Stigma*.—Color: RHS 153C (Strong greenish yellow).
*Petal*.—Length in relation to width: Moderately longer. Color of upper side: RHS NN155C (White). Color of under side: RHS NN155C (White). Shape: Orbicular. Apex: Rounded. Base: Concavo-convex. Margin: Entire.
*Sepal*.—Length (sepal tip to point of attachment to receptacle): 24.5 mm. Width: 14.2 mm. Color: RHS 137B (Moderate olive green). Shape: Oval. Apex: Convex. Margin: Entire.
Flowering:
*Time of beginning of flowering*.—Very early.
*Flowering interval*.—Mid-November to mid-May.
Fruit:
*Size*.—Medium. Length: 48.3 mm. Width: 36.6 mm. Length/width ratio: 1.32. Length in relation to width: Moderately longer.
*Soluble solids in °Brix*.—6.
*Weight*.—27.1 grams.
*Fruit hollow*.—Length: 16.34 mm. Width: 3.56 mm. Hollow length/width ratio: 4.56.
*Shape*.—Conical.
*Difference in shape of terminal and other fruits*.—None or very slight.
*Fruit color*.—RHS 45A (Vivid red).
*Evenness of color*.—Even or very slightly uneven.
*Glossiness*.—Medium.
*Evenness of surface*.—Even or very slightly uneven.
*Width of band without achenes*.—Absent or very narrow.
*Position of achenes*.—Below surface.
*Achene color*.—RHS 146C (Moderate yellow-green).
*Position of calyx attachment*.—Level with fruit.
*Attitude of sepals*.—Upwards.
*Diameter of calyx in relation to diameter of fruit*.—Slightly larger.
*Adherence of calyx*.—Strong.
*Color of flesh* (*excluding core*).—RHS 44A (Vivid reddish orange).
*Evenness of color of the flesh*.—Even.
*Distribution of flesh color*.—Marginal and central.
*Color of core*.—RHS 44C (Vivid reddish orange).
*Fruiting*.—Time of beginning of fruit ripening: Very early. Harvest interval: Mid-December to mid-May. Type of bearing: Not remontant. Productivity: 1.4 kg to 1.7 kg of fruit per plant per season from 6.5-month-old plants when grown in Rociana, Huelva, Spain.
*Shipping and storage characteristics* (*post-harvest characteristics*).—Following harvest, fruit can be stored for 7-9 days if maintained under cooled temperatures that are standard for strawberry storage.
Resistance to pests:
*Powdery mildew* (*Podosphaera macularis*).—Moderately susceptible.

COMPARISON WITH PARENTAL AND COMMERCIAL VARIETIES

'DrisStrawEightyFour' differs from the proprietary female parent '974AC033' (unpatented) in that 'DrisStrawEightyFour' has a larger plant, smaller fruit, and better post-harvest qualities than '974AC033'.

'DrisStrawEightyFour' differs from the proprietary male parent 'ES089.028' (unpatented) in that 'DrisStrawEightyFour' has an earlier maturity and a larger fruit size than 'ES089.028'.

'DrisStrawEightyFour' differs from the commercial variety 'Florida Radiance' (U.S. Plant Pat. No. 20,363), also known as 'Florida Fortuna', in that 'DrisStrawEightyFour' has a shorter and wider plant, less serrations per terminal leaflet, and inflorescence above foliage, whereas 'Florida Radiance' has a taller and narrower plant, more serrations per terminal leaflet, and inflorescence below foliage.

'DrisStrawEightyFour' differs from the commercial variety 'DrisStrawTwentySeven' (U.S. Plant Pat. No. 23,400) in that 'DrisStrawEightyFour' has dense foliage, crenate margins on terminal leaflets, an absent or very narrow width of band without achenes on fruit, and an absent or small fruit cavity, whereas 'DrisStrawTwentySeven' has medium density of foliage, serrate margins on terminal leaflets, a very broad width of band without achenes on fruit, and a large fruit cavity.

We claim:

1. A new and distinct variety of strawberry plant named 'DrisStrawEightyFour' as shown and described herein.

* * * * *